United States Patent
Westrum, Jr. et al.

[11] Patent Number: 5,512,033
[45] Date of Patent: Apr. 30, 1996

[54] MALLEABLE PENILE PROSTHESIS

[75] Inventors: John W. Westrum, Jr., Prior Lake; Mark S. Chace, St. Anthony; Charles C. Kuyava, Eden Prairie, all of Minn.

[73] Assignee: American Medical Systems, Inc., Minnetonka, Minn.

[21] Appl. No.: 287,439

[22] Filed: Aug. 8, 1994

[51] Int. Cl.$^6$ ..................................................... A61F 2/26
[52] U.S. Cl. ........................................................ 600/40
[58] Field of Search .............................. 600/38–41, 29, 600/30; 623/11, 66

[56] References Cited

U.S. PATENT DOCUMENTS

| | | |
|---|---|---|
| 3,987,789 | 10/1976 | Timm et al. . |
| 4,392,568 | 7/1983 | Burton et al. . |
| 4,594,998 | 6/1986 | Porter et al. . |
| 4,665,902 | 5/1987 | Goff et al. . |
| 4,666,428 | 5/1987 | Mattioli et al. . |
| 4,669,456 | 6/1987 | Masters . |
| 4,807,608 | 2/1989 | Levius . |
| 4,881,531 | 11/1989 | Timm et al. . |
| 4,988,357 | 1/1991 | Koss ............................. 600/40 |
| 5,050,592 | 9/1991 | Olmedo ......................... 600/40 |

OTHER PUBLICATIONS

"AMS Malleable 600™" American Medical Systems Publication 30915, 1983.

Primary Examiner—Angela D. Sykes
Assistant Examiner—Samuel Gilbert
Attorney, Agent, or Firm—Peter C. Richardson; Larry C. Akers; Mark Dryer

[57] ABSTRACT

A malleable penile prosthesis adapted to be implanted in a corpus cavernosum of a penis comprising an elongated core which is bendable about its longitudinal axis with the capability of holding the configuration to which it is bent and is substantially rigid when in the unbent straight configuration, a sleeve of braided biocompatible material, having an inner surface and an outer surface, enveloping the core with the inner surface of the sleeve in contact with the core and the sleeve and core being accommodated within an outer tube of elastomeric material, which tube has a substantially rounded smooth outer surface and an inner surface having a profile formed of alternate grooves and ribs in a substantially helical arrangement. A method of forming a malleable prosthesis is also disclosed.

6 Claims, 3 Drawing Sheets

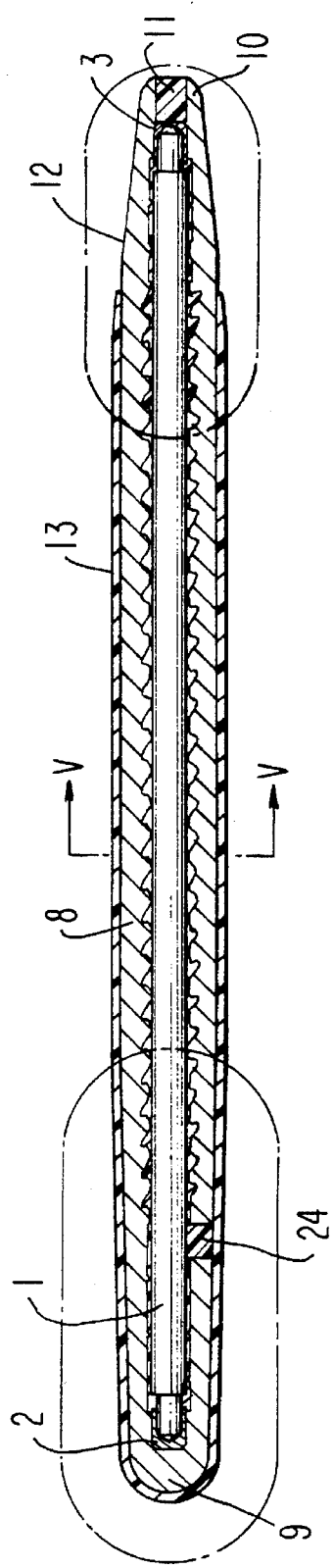
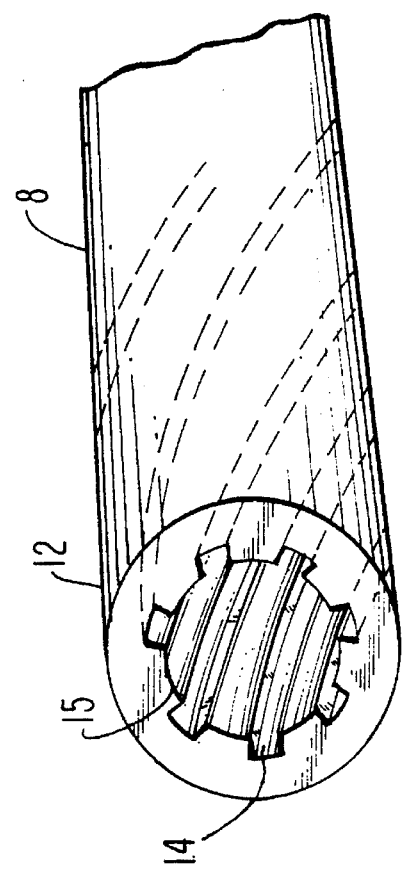
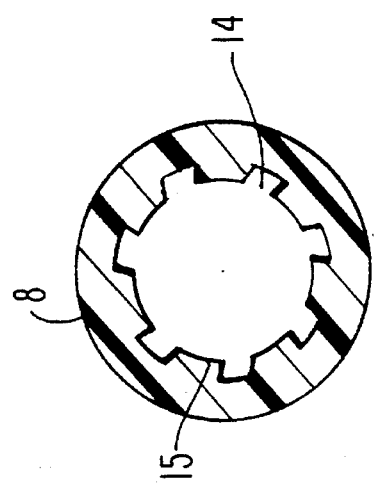

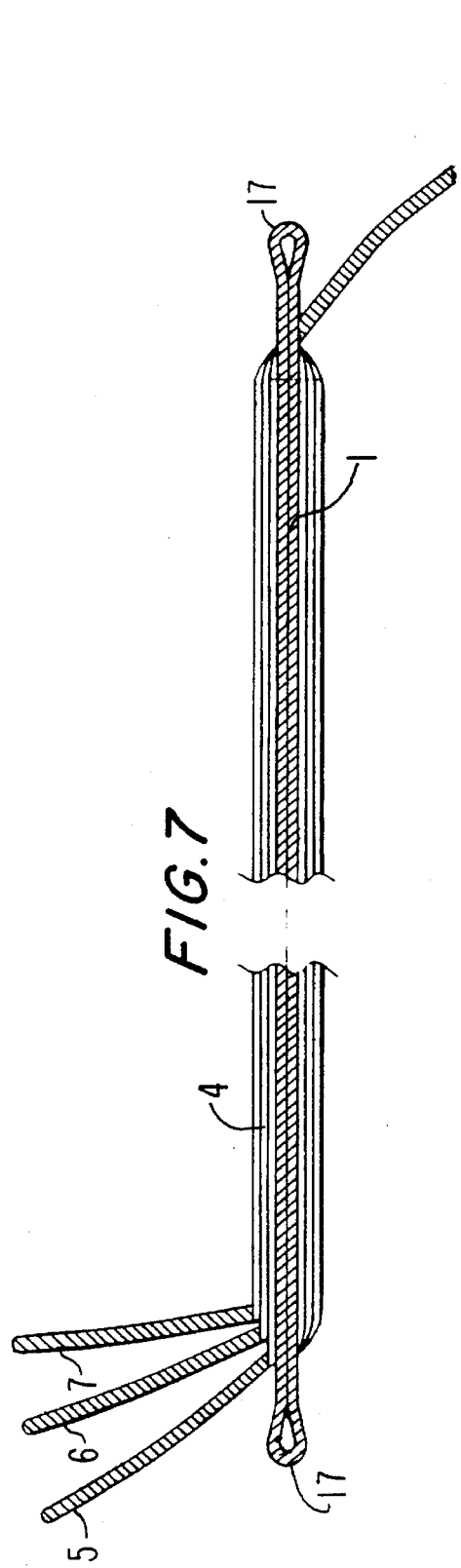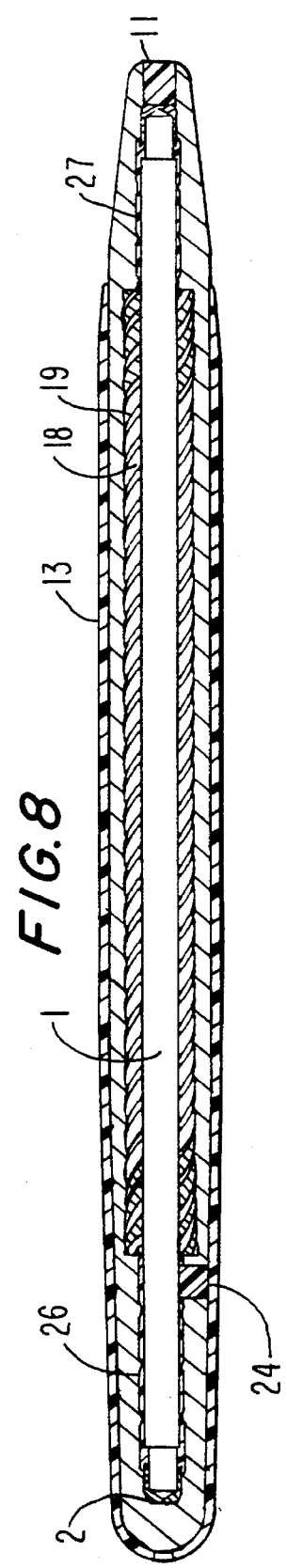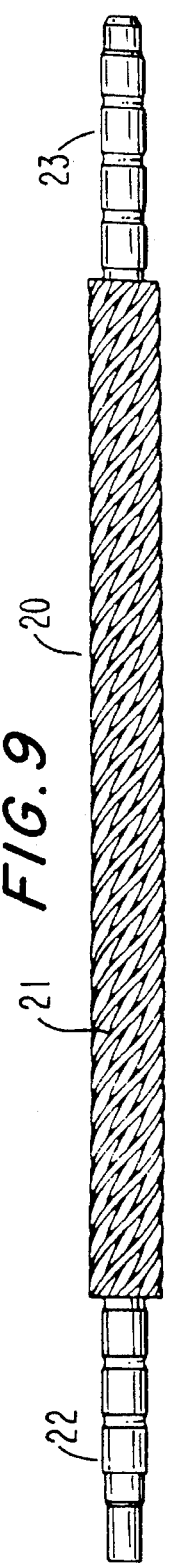

MALLEABLE PENILE PROSTHESIS

FIELD OF THE INVENTION

This invention relates to a malleable penile prosthesis. More particularly, the invention is concerned with a penile prosthesis comprising a malleable core enveloped in a sleeve, which sleeve and core are accommodated within an outer tube of elastomeric material. The invention also relates to a method of making a malleable penile prosthesis. All the materials used in the prosthesis are biocompatible.

As used herein the term "malleable" means bendable, with the capacity of holding the resulting configuration until a subsequent step of bending or straightening is performed. The malleable core of the prosthesis of this invention additionally has the characteristic of being substantially rigid when not being subjected to bending, and particularly when in the unbent straight configuration.

BACKGROUND OF THE INVENTION

Impotence or inability to achieve penile erection is quite prevalent and many solutions have been proposed and are available in the art to cure or compensate for the condition. In particular, various types of penile prostheses are commercially available.

The majority of penile prostheses fall into two types. These two types are the inflatable, implantable prosthesis and the simple implantable inherently stiff or substantially rigid prosthesis. The inflatable prosthesis is normally implanted in pairs within the corpora cavernosa and connected to hydraulic pumping means, also implanted within the patient's body, which means enable the prosthesis to be inflated for erection and deflated for flaccidity. The simple or non-inflatable, prosthesis is also generally implanted in pairs in the corpora cavernosa and, in view of its inherent stiffness, provides a generally constant erection. Hence, it is desirable to provide positionability so that the erection may be at least partially concealed by the patient. Positionability is generally achieved by making the simple prosthesis bendable or malleable and the prosthesis provided by the present invention is of this simple type, herein designated as a malleable prosthesis.

A number of prior art prostheses deal with the requirement of positionability by providing various forms of segmented or articulated structures. Such structures are disclosed, for example, in U.S. Pat. Nos. 4,665,902; 4,666,428 and 4,807,608 and 4,881,531.

Another form of positionable prosthesis comprises an elastomeric rod and a metal wire coil coaxially embedded within at least a portion of the rod, as disclosed in U.S. Pat. No. 4,669,456.

U.S. Pat. No. 4,392,562 discloses a limited bend malleable penile prosthesis comprising an elongated malleable element having bend limiting means comprising a plurality of engageable adjacent elements positioned in co-operative juxtaposition with said malleable element.

U.S. Pat. No. 3,987,789 discloses a malleable penile prosthesis comprising an elongated malleable rod portion housed within a generally tubular, physiologically inert plastic body; and U.S. Pat. No. 4,594,998 discloses a similar type of prosthesis but having a somewhat more elaborate and improved structure.

U.S. Pat. No. 4,988,357 discloses a penile prosthesis comprising an implantable flexible rod member formed by a core portion comprising a plurality of metallic wires, typically high-purity silver, and an outer casing comprising implantable plastic material around the core portion.

It has now been found that an improved malleable penile prosthesis of the type having a malleable core accommodated within a tubular sheath may be provided as hereinafter described, which prosthesis has improved positionability and improved performance.

SUMMARY OF THE INVENTION

In accordance with the invention there is provided a malleable penile prosthesis adapted to be implanted in a corpus cavernosum of a penis comprising an elongated core having an unbent straight configuration about a longitudinal axis, a distal end and a proximal end, which core is bendable about said axis with the capability of holding a configuration to which it is bent and is substantially rigid when in the unbent straight configuration, a sleeve of braided biocompatible material, having an inner surface and an outer surface, enveloping said core with the inner surface of the sleeve in contact with the core and an outer tube of elastomeric material containing the sleeve and core, said tube having a wall with an outer surface and an inner surface, a distal end and a proximal end, each of said ends having a substantially rounded smooth outer surface, said outer surface of the wall being substantially smooth and said inner surface having a profile formed of alternate grooves and ribs in a substantially helical arrangement.

In a preferred embodiment of the prosthesis according to the invention the core is formed from a plurality of metal wires, especially stainless steel wires, twisted together and secured at each end with a solid metal cap to form an integral malleable element.

Preferably the sleeve enveloping the core comprises a plurality of layers, preferably three, of braided polymeric material. While the outside diameter of the sleeve is matched with the internal diameter of the outer tube as defined by the crests of the ribs in the inner surface of the wall of the outer tube, there is a small clearance, of the order of 0.010 to 0.050 inch, between the outer surface of the sleeve and the surfaces of said crests when the prosthesis is in a straight configuration. The stated surfaces tend to come into contact with each other when the prosthesis is subjected to bending. The small clearance contributes toward positionability without kinking.

A preferred material for the braided sleeve is a biocompatible polyester, particularly polyethylene terephthalate.

The invention also provides a method of forming a malleable penile prosthesis comprising an elongated core, a sleeve enveloping said core and an outer tube accommodating said sleeve and core, which method comprises forming said core, enveloping said core with a sleeve of braided biocompatible material, forming a tube of elastomeric material having a wall with an inner surface and an outer surface and a bore defined by the inner surface of the wall, which inner surface has a profile formed of alternate grooves and ribs in a substantially helical arrangement, and inserting said sleeve and core within said bore so that the crest of each rib is matched closely to the outer surface of the sleeve. The close matching of the outer surface of the sleeve with the inner surface of the outer tube so as to leave a small clearance between said surfaces when the prosthesis is in a straight configuration provides a prosthesis with column strength, positionability and natural feel.

In performing the method of the invention the elongated core is preferably formed by twisting together a plurality of metal wires, initially positioned in side-by-side longitudinal relationship, to form a substantially rigid but bendable integral bundle having a distal end and a proximal end, and securing the integrity of said core by crimping a solid metal cap to each end of the twisted bundle of metal wires.

Preferably, the sleeve of braided material comprises a plurality of layers of braided polymeric material and the sleeve is positioned around the core by braiding the layers, preferably three, tightly around the core to form an integral sleeve in intimate contact with the core.

DETAILED DESCRIPTION OF THE INVENTION

The prosthesis of the invention comprises, in combination, a malleable core enveloped in a sleeve of braided material and an outer tube of elastomeric material having an internal surface with a distinctive profile.

Although a fewer number of wires with consequential larger diameter may be used, in a preferred embodiment the core is made by twisting together a plurality of metal wires, for example from 100 to 150 wires, each having a diameter of from 0.006 to 0.010 inch. A particularly preferred embodiment comprises a core made from 134 wires of stainless steel, each having a diameter of about 0.008 inch.

The metal wires are typically made by drawing and usually are of circular cross-section, both for ease of fabrication and interactive contact. However, other configurations, for example, uniform hexagons, are possible, providing the resulting bundle has the required positionability after twisting.

Twisting of the bundle of wires is necessary to provide positionability without kinking or other distortion and to overcome resistance to bending. The proper degree of twisting to achieve optimum positionability and cycle life may be determined by the lay of the wire and is preferably of the order of 1.45 to 1.65 inches.

Stainless steel is the metal of choice for the wires over other metals or alloys which might be used because it possesses a combination of desirable characteristics. Thus, it is preferred over, for example, silver, tantalum, an alloy of titanium, aluminum and vanadium, and chromium-nickel super alloy, which metals and alloys have been suggested for malleable prostheses.

The other metals and alloys mentioned above tend to exhibit either more wire-to-wire galling, i.e., friction interaction, than stainless steel, or other loss in positionability and/or cycle life.

The preferred twisted wire core described above has better wire-to-wire interaction than previous assemblies incorporating metal wires. By using a greater number of wires, of smaller diameter, than used hitherto and controlling the degree of twist of the wires with little work-hardening a great improvement in positionability is obtained. This, together with increased wire-to-wire contact while maintaining an extended cycle life provides an improved malleable core.

The malleable core is enveloped in a sleeve of braided material, preferably a biocompatible polyester, such as polyethylene terephthalate.

In a preferred embodiment the braid is formed from a yarn of about 200–250 denier, 50 filament, 2-ply braided on 16 carriers having 43–50 picks per inch with improved tightness over prior braids. The sleeve preferably comprises three layers of the braid, and the new sleeve is a distinct improvement over prior art sleeves.

The core enveloped in the sleeve is accommodated within an outer tube made of elastomeric material, for example, silicone rubber. The outer tube has a distal end and a proximal end, each of which has a substantially rounded smooth outer surface. The outer tube defines a central longitudinal bore which, to facilitate formation of the prosthesis, initially has an open side port set back from the distal end and is open at the proximal end. The proximal open end allows insertion of the core and sleeve therethrough, as well as withdrawal of the groove-forming mandrel, which withdrawal is aided by the open side port, as hereinafter described. After formation of the prosthesis the open side port and proximal open end are sealed by filling with a silicone adhesive.

The outer tube has a wall with a substantially smooth outer surface and an inner surface having a profile formed of alternate grooves and ribs in a substantially helical arrangement. When the sleeve-covered core is accommodated within the outer tube there is a small clearance between the crest of each rib on the inner surface of the wall of the tube and the outer surface of the sleeve. When the prosthesis is subjected to bending each crest in the proximity of the bend tends to come into touching contact with the outer surface of the sleeve. The preferred manner in which the grooves and ribs are formed on the inner surface of the wall of the outer tube is described hereinafter.

BRIEF DESCRIPTION OF THE DRAWINGS

Preferred embodiments of the invention are illustrated in the accompanying drawings, in which:

FIG. 1 is a side elevation, partly in section, of one embodiment of a prosthesis according to the invention;

FIG. 5 is a cross-section, partly enlarged, through line V—V of FIG. 1 without the outer sheath;

FIG. 6 is a view of the inside of the outer tube of the embodiment of FIG. 1 showing the helical arrangement of the ribs and grooves;

FIG. 7 is a side elevation, partly in section of the core and sleeve during formation thereof;

FIG. 8 is a side elevation, partly in section, of another embodiment; and

FIG. 9 is a side elevation of a mandrel used in the formation of the embodiment of FIG. 8.

FIG. 1 of the accompanying drawings illustrates one embodiment of a prosthesis according to the invention. The prosthesis comprises a central core 1 extending about the longitudinal axis of the prosthesis.

The core is made from a plurality of metal wires twisted together and secured to form an integral element by metal caps at the distal end 2 and proximal end 3 of the core.

Figure 2:
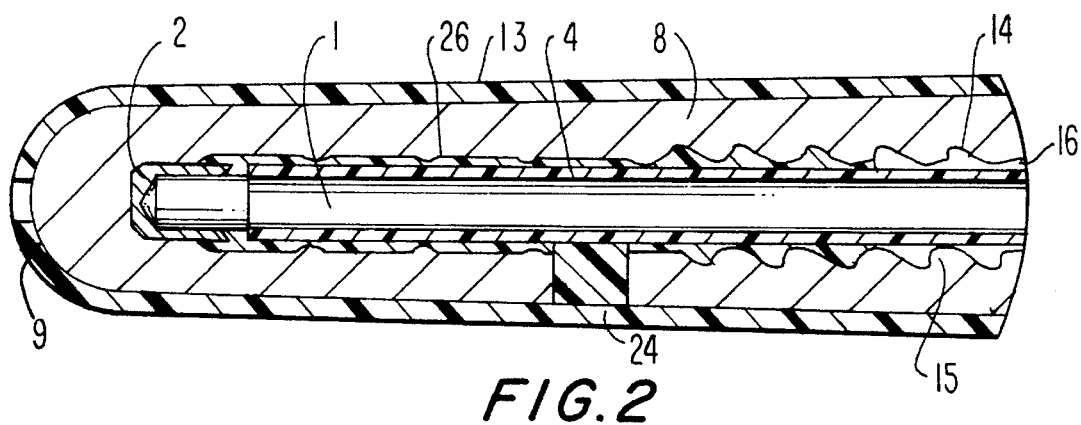
FIG. 2 is an enlarged sectional side view of the distal portion of the embodiment of FIG. 1.
Figure 3:
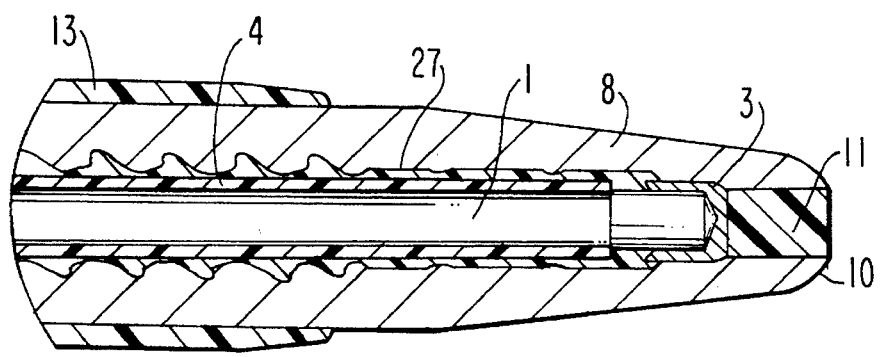
FIG. 3 is an enlarged sectional side view of the proximal portion of the embodiment of FIG. 1.

The metal wire malleable core 1 is enveloped in a sleeve 4 (See FIG. 2, 3 and 4) made up from three layers of braided material, preferably a polyester much as polyethylene terephthalate. As shown in FIG. 7 the three layers 5, 6, 7 of material are braided around the core in situ.

The core/sleeve combination is accommodated within an elongated outer tube 8 having a substantially rounded smooth surface distal end 9 and a substantially rounded smooth surface proximal end 10.

The elongated outer tube has a central bore which accommodates the core and sleeve. The end of the bore at the proximal end 10 of the tube is open during formation of the prosthesis (as described hereinafter) and is closed with a plug of adhesive 11, preferably silicone, when the prosthesis is completed.

The outer surface 12 of the wall of the tube 8 is substantially smooth. In a preferred embodiment of the invention the outer tube is enveloped in an outer sheath 13 of elastomeric material. This outer sheath is useful for increasing the diameter of the prosthesis. The inner surface of the wail of the tube has a profile formed of alternate grooves 14 and ribs 15. There is a small clearance 16 (FIG. 2) between the crest of each rib and the outer surface of the sleeve 4 and this clearance allows bending and straightening of the prosthesis without kinking of the wire bundle while restricting bending to a desirable limit. The alternate grooves 14 and ribs 15 are formed in a substantially helical arrangement as illustrated for example in FIG. 6.

The outer tube 8 is made from a moldable elastomer, for example a silicone rubber, and the groove/rib profile is formed by compression moulding over a preformed mandrel at an elevated temperature, for example, about 117° C.

The helical grooves are preferably at an angle of about 45° and are formed from a seven start mould mandrel, which provides a seven-start structure of helical grooves. which has been found to be the optimum number for longitudinal rigidity and lateral strength. The width and depth of the grooves and ribs are balanced so as to provide optimum stiffness and bendability and the helical profile gives a more natural feel to the prosthesis without detracting from the bendability.

The braided sleeve contributes to the positionability of the malleable core, and the use of three layers in the braid has been found to be enough to contain the wires in the core and to match the outer diameter of the sleeve with the inner diameter of the helix, defined by the crests of the ribs.

Referring to FIG. 7 of the drawings the malleable core is formed by assembling a plurality of metal wires, preferably about 134 wires of stainless steel, each having a diameter of about 0.008 inch, in side-by-side relationship, forming each end of the wire bundle into a loop 17 to enable the assembly to be connected to a suitable twisting apparatus, for example a lathe, so that the wires may be twisted together.

When the desired degree of twisting for optimum performance has been achieved, the core is removed from the twisting apparatus, the sleeve is braided around the core and the loops at each end are removed so that each end may be capped to secure the twisted wires.

The sleeve covered core 1 is then inserted into the central bore of the outer tube through the open end at the proximal end of the tube and the open end is then closed with a plug of adhesive silicone 11 to complete the desired prosthesis.

A preferred embodiment of the prosthesis according to the invention is illustrated in FIG. 8. In this embodiment the various features are substantially similar to those of the embodiment illustrated in FIG. 1 but the helical arrangement of grooves 18 and ribs 19 is slightly modified.

The grooves and ribs of the outer tube of the embodiment of FIG. 8 are formed by moulding about a mandrel 20 such as that illustrated in FIG. 9. The mandrel comprises an elongated groove and rib forming main portion 21, a distal end portion 22 and a proximal end portion 23.

Figure 4:
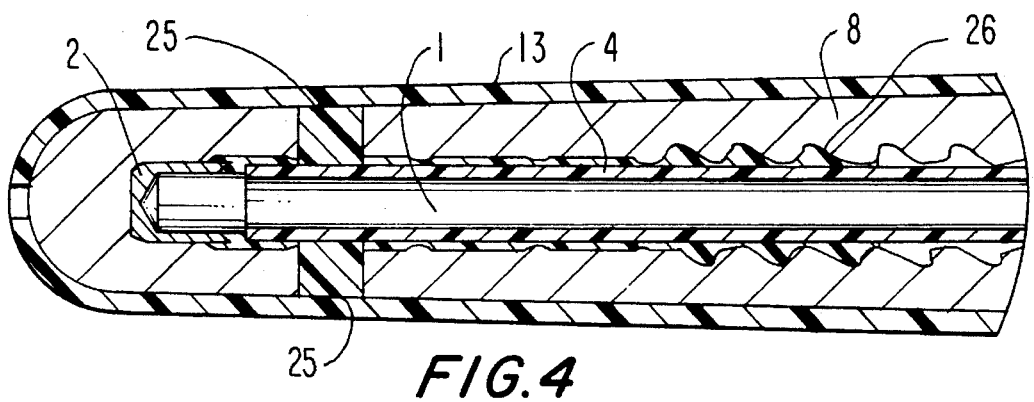
FIG. 4 is an enlarged sectional side view of an alternative version of the distal portion of a prosthesis according to the invention.

The outer tube is formed by compression moulding, at an elevated temperature of a suitable elastomeric polymer, for example, silicone rubber, over the mandrel. The moulding operation forms the outer tube with a longitudinal bore which matches the profile of the mandrel wherein the inner surface of the central portion has a helical arrangement of grooves and ribs. The moulded tube is provided with an open hole or port 24 in a side wall of the distal portion. In an alternative embodiment, as illustrated in FIG. 4, the hole or port 25 extends diametrically across the tube. The bore has an open end 11 at the proximal portion of the tube, formed by the proximal portion 23 of the mandrel.

When the moulding operation is completed an air pipe is attached to the hole 24 or 25 and the bore is distended by air pressure so that the mandrel may be removed through the open proximal end of the bore, and the formed outer tube is then allowed to cool. The malleable core and sleeve is then placed in the bore and anchored to prevent internal twisting by adhesive 26 at the distal end and adhesive 27 at the proximal end. The holes 24 or 25 at the distal end and the hole 11 at the proximal end are filled with adhesive to complete the formation of the prosthesis.

We claim:

1. A malleable penile prosthesis adapted to be implanted in a corpus cavernosum of a penis comprising an elongated core having an unbent straight configuration about a longitudinal axis, a distal end and a proximal end, which core is bendable about said axis with the capability of holding a configuration to which it is bent and is substantially rigid when in the unbent straight configuration, a sleeve of braided biocompatible material having an inner surface and an outer surface enveloping said core with the inner surface of the sleeve in contact with the core and an outer tube of elastomeric material containing the sleeve and core, said tube having a wall with an outer surface and an inner surface, a distal end and a proximal end, each of said ends having a substantially rounded smooth outer surface, said outer surface of the wall being substantially smooth and said inner surface having a profile formed of alternate grooves and ribs in a substantially helical arrangement.

2. A prosthesis according to claim 1, in which said core is formed from a plurality of metal wires twisted together and secured at each of said core distal end and core proximal end with a solid metal tip to form an integral malleable element.

3. A prosthesis according to claim 2, in which said sleeve comprises a plurality of layers of braided polymeric material having an outside diameter which matches an internal diameter defined by crests of the ribs in the outer tube, said crests having surfaces, small clearance being provided between the outer surface of the sleeve and the surfaces of said crests when the prosthesis is in a straight configuration.

4. A prosthesis according to claim 3, in which the core comprises about 100 to 150 wires of stainless steel each having a diameter of from about 0.006 to 0.010 inch, twisted together and being enveloped in a sleeve comprising at least three layers of braided polyester.

5. A prosthesis according to claim 1, in which the grooves in the inner surface of the wall of the outer tube are defined by a seven-start structure of helical grooves having a helix angle of about 45° and the elastomeric material of the tube is a silicone rubber.

6. A prosthesis according to claim 1, in which an outer sheath envelopes the outer tube.

* * * * *